United States Patent
Hildebrandt

(10) Patent No.: US 6,321,388 B1
(45) Date of Patent: Nov. 27, 2001

(54) ARTICLE OF CLOTHING AND AN ORTHOPEDIC DEVICE THEREFOR

(76) Inventor: Hans-Dietrich Hildebrandt, Hohlesteinweg 16, 34292 Ahnatal (DE)

( * ) Notice: Subject to any disclaimer, the term of this patent is extended or adjusted under 35 U.S.C. 154(b) by 0 days.

(21) Appl. No.: 09/595,106

(22) Filed: Jun. 16, 2000

(30) Foreign Application Priority Data

Jun. 18, 1999 (DE) .......................................... 299 11 206 U

(51) Int. Cl.⁷ .................................................. A41D 13/00
(52) U.S. Cl. .............................................. 2/69; 2/94; 450/1
(58) Field of Search ................................ 2/69, 105, 115, 2/106, 113, 114, 102, 94, 95, 108, 44, 45, 92, 455, 456, 467; 128/99.1, 106.1, 101.1, 107.1, 111.1; 602/19, 7; 450/1

(56) References Cited

U.S. PATENT DOCUMENTS

| | | |
|---|---|---|
| 3,521,623 | 7/1970 | Nichols . |
| 3,868,952 | 3/1975 | Hatton . |
| 4,120,297 | 10/1978 | Rabischong . |
| 4,926,502 | 5/1990 | Miyamura . |
| 5,034,998 * | 7/1991 | Kolsky ....................................... 2/465 |
| 5,052,052 * | 10/1991 | Gilford et al. ............................ 2/467 |
| 5,054,127 * | 10/1991 | Zevchak .................................... 2/247 |
| 5,381,558 * | 1/1995 | Lo ............................................. 2/115 |
| 5,551,085 * | 9/1996 | Leighton .................................... 2/44 |
| 5,571,076 * | 11/1996 | Cooper .................................... 602/19 |
| 5,724,993 | 3/1998 | Dunfee . |
| 5,768,717 * | 6/1998 | Sueur ....................................... 2/467 |
| 5,806,093 * | 9/1998 | Summers .................................. 2/69 |
| 5,978,965 * | 11/1999 | Summers .................................. 2/69 |

FOREIGN PATENT DOCUMENTS

| | | |
|---|---|---|
| 0 461 319 A | 12/1991 | (EP) . |
| 0 479 014 A1 | 4/1992 | (EP) . |

* cited by examiner

Primary Examiner—Gloria M. Hale
(74) Attorney, Agent, or Firm—Michael J. Striker

(57) ABSTRACT

The invention relates to an article of clothing for osteoporosis treatment. The article of clothing is comprised of a flexible, stretchable material and has a front part (2) and a back part (3), which is provided on its inside with at least one air cushion strip (6) on each side of an imaginary center line (5) associated with the vertebral column of a user, each of these strips extending over the thoracic vertebral region and possibly also the upper lumbar vertebral region and having a number of air chambers that communicate with one another (FIG. 1).

13 Claims, 2 Drawing Sheets

ARTICLE OF CLOTHING AND AN ORTHOPEDIC DEVICE THEREFOR

BACKGROUND OF THE INVENTION

The invention relates to an article of clothing made of a flexible, stretchable material and an orthopedic device for it.

Up to now, the treatment of people suffering from osteoporosis has not been satisfactory in every regard. Osteoporosis, which mostly occurs in women, attacks the skeletal system by causing the loss of bone mass. Although osteoporosis can be caused among other things by metabolic disorders, inactivity, and cortisone treatment, its chief cause is considered to be an age-related deficiency in anabolic hormones (estrogens), which are required for the production of bone tissue. One result of this deficiency is that the bone tissue gradually breaks down, the bone trabeculae become thinner and finally dissolve, and an increased fracture tendency arises.

In the region of the vertebral column, osteoporosis leads to the development of a hollow hump-back. Since the thoracic vertebrae are weak in the hump region in which they are under stress, vertebral fractures occur, which result in a formation of wedge-shaped vertebrae and thereby an increased acuteness of the hump region. In the hollow region, however, fewer fractures are observed because in this region, predominantly the posterior, comparatively hard vertebral regions are stressed.

At present, predominantly hormone and medication therapies are used to slow or prevent osteoporosis by means of supplying the patients with the missing estrogens and other substances (e.g. calcium, sodium fluoride, biphosphonates), which aid in bone production or reduce bone decomposition. In order for these substances to travel to the bones via the bloodstream and to be effective there, these therapies are frequently combined with special circulation promoting exercises. But the therapeutic successes that can be achieved in this way are not satisfactory. The exercises are also intended to strengthen the musculature in order to counteract the hollow hump-back.

In addition, so-called lumbosacral truss pads have been disclosed (EP 0 479 014 A1), which are attached to support bandages or belts and are made of air cushions which have a large number of air chambers which communicate with one another by means of partially discontinuous seams. Truss pads of this kind are used for the purpose of tensing the abdominal, gluteal, and ischiocrural musculature through reflex muscular work and to relax the spinal extensor musculature and thus to right the pelvis and as a result, to produce a stretching of the lumbar lordosis and thoracic kyphosis, i.e. a stretching of the vertebral column as a whole. The wearing of such a truss pad can be used to counteract osteoporosis as long as a hollow hump-back is not yet fixed because then, the formation of a hollow hump-back and vertebral fractures particularly in the vicinity of the thoracic vertebrae can still be counteracted.

Consequently, with the aid of the known lumbosacral truss pads, in particular the mechanoreceptors of the lumbar region can be stimulated and the relevant muscles can be activated in order to improve posture. A normalization of the vertebral column structure produced by means of this, however, can neither stop the loss of bone mass and bone architecture, nor in the long term halt the osteoporosis or entirely prevent its most significant consecutive symptom, namely the occurrence of vertebral fractures.

SUMMARY OF THE INVENTION

The object of the invention is to produce a means with which the circulation of the bones in the region of the lumbar and thoracic vertebral column can be promoted and as a result, there can be an improvement in the action of combination therapies made up of medications and exercises.

This object is attained according to the invention by means of the features of the article of clothing for osteoporosis treatment being made from a flexible, stretchable material and comprising: a front part, a back part having an inner side and an imaginary center line associated with a verbal column of a user, and at least two air cushion strips extending over a thoracic vertebral region of said user, wherein one of said cushion strips is on one side of said imaginary center line and another one of said cushion strips is on another side of said imaginary center line and wherein each of said cushion strips has a plurality of air chambers being separated from one another by means of discontinuous seams such that said air chambers communicate with one another.

DESCRIPTION OF THE PREFERRED EMBODIMENT

Figure 1:
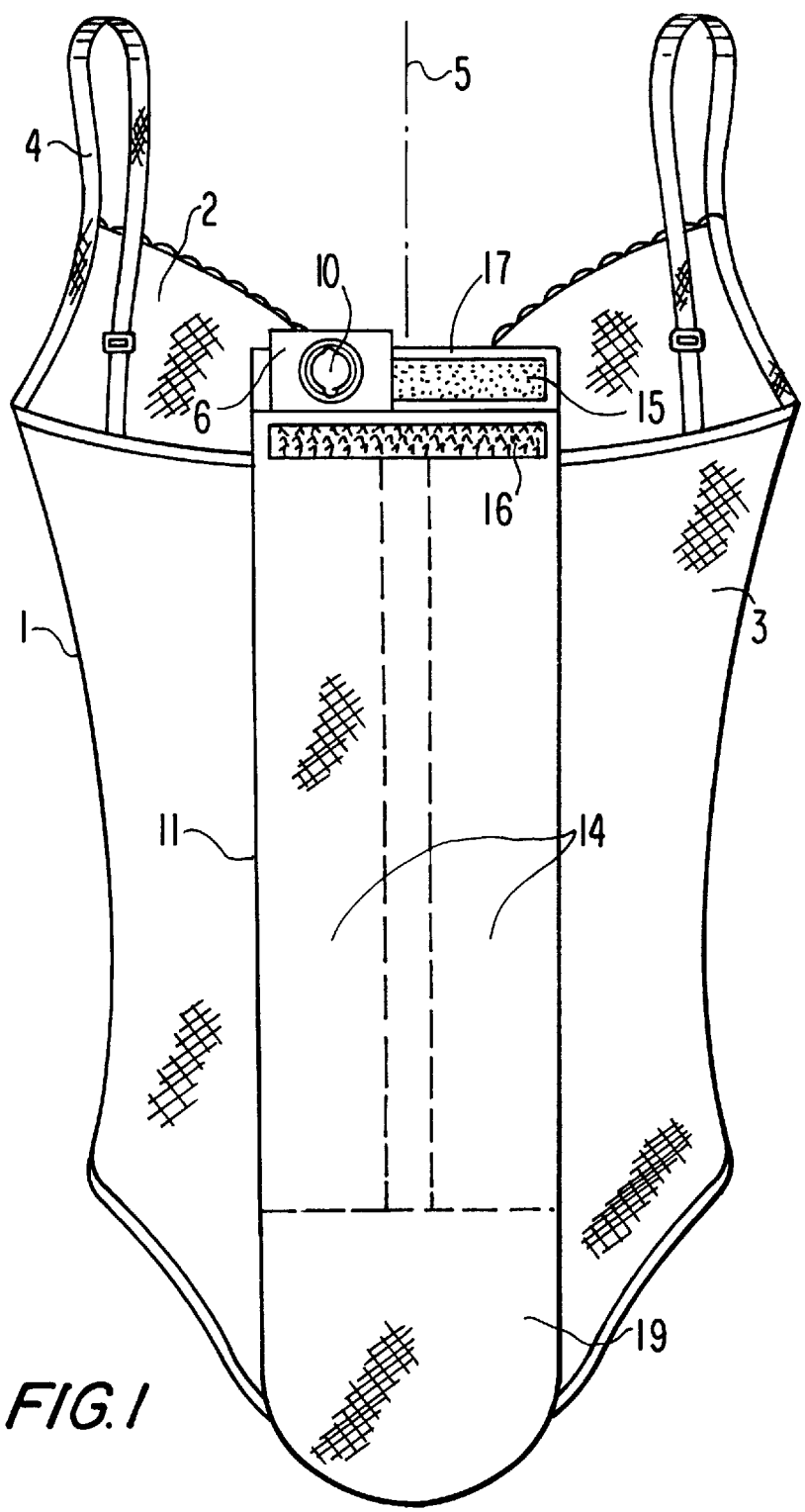
FIG. 1 shows a simple schematic view of an article of clothing according to the invention which is suitable for the treatment of osteoporosis.

FIG. 1 shows an article of clothing 1 in the form of an only schematically indicated corselet made of a flexible material. The article of clothing 1 has a front part 2 and a back part 3 connected to it. In the view according to FIG. 1, the article of clothing 1 is shown turned inside out and is depicted so that in particular the inside of the back part is visible. The article of clothing 1 can also be provided with conventional supports 4. In the lower region, the front part 2 and a back part 3 are connected to each other, producing a trouser part with leg openings.

According to FIG. 1, on the inside of the back part 3, on both sides of a center line 5, which runs essentially along the vertebral column of the patient when the article of clothing 1 is being worn, at least one air cushion strip 6 is provided, which respectively extends over those regions of the back part 3 which rest against the thoracic vertebral region and preferably also the upper lumbar vertebral region of the patient when the article of clothing 1 is being worn.

Figure 2:
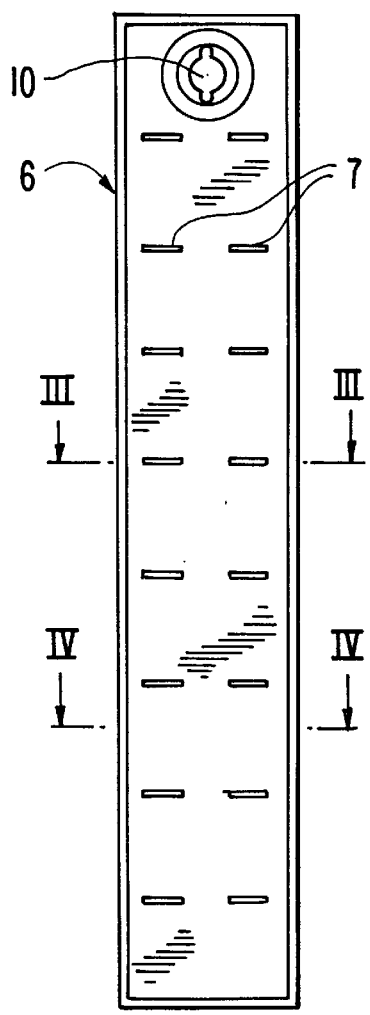
FIG. 2 shows a top view of an air cushion strip for the item of clothing according to FIG. 1 in a slightly larger scale.
Figure 3:
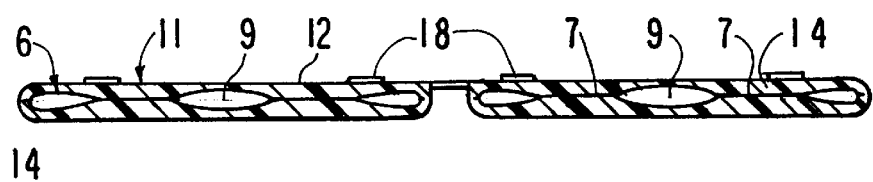
FIGS. 3 and 4 show cross sections through an orthopedic device that is provided with air cushion strips and can be attached to the article of clothing according to FIG. 1, in the vicinity of the intersecting lines III—III and IV—IV in FIG. 1 and in an even further enlarged scale.
Figure 4:
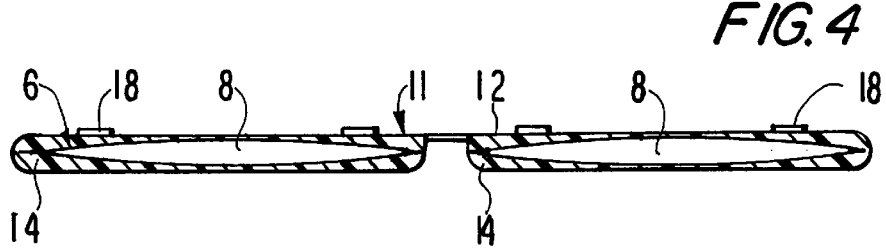

According to FIGS. 2 to 4, each air cushion strip 6 is comprised of a cushion that is closed on its outer circumference and has an essentially rectangular contour. By means of a number of seams 7, which extended, for example, parallel to the short rectangular sides, the air cushion is divided into a number of air chambers 8 (FIG. 4) which are disposed one after the other in the direction of the long sides and all communicate with one another by means of breaks 9 (FIG. 3) that pass through the seams 7. In addition, each air cushion strip 6 has a connection fitting 10, which is provided with a closure, is designated for inflating the air cushion strip 6, and is situated in a location that does not create discomfort when the article of clothing is being worn.

Preferably, an orthopedic device 11, which is depicted in a simple schematic form in FIGS. 1, 3, and 4, is used to attach the air cushion strip 6 to the back part 3. This orthopedic device includes a flexible carrier 12, which is made of a textile material that is preferably not irritating to the skin and has an essentially rectangular contour. On its front face and on both sides of a center line disposed between the long rectangle sides, the carrier 12 has two pockets 14 which are of a size that corresponds to the size of the air cushion strips 6 and preferably in their upper ends, are provided with closure elements 15, 16, which are comprised, for example, of complementary hook-and-loop strips that are attached to the insides of pocket flaps 17 and the outsides of the pockets 14 respectively and cooperate in the usual manner when the pockets 14 are closed. On the back face, the carrier 12 is provided with means 18 (FIGS. 3, 4) for being fastened to the back part 3 of the article of clothing 1. These means 18 can likewise be embodied as hook-and-loop strips that cooperate with complementary hook-and-loop strips fastened to the inside of the back part 3 by means of being sewn or the like.

In a suitable fashion, an air cushion strip 6 is already inserted into each of the pockets 14 by the manufacturer so that the connection fitting 10 can be accessed from the side of the pocket flaps 17. In this way, the patient can choose whether she would like to purchase a finished article of clothing 1 already provided with the air cushion strips 6 or purchase only the device 11 and attach it, possibly herself, to an article of clothing 1 of her own choosing.

When the article of clothing 1 according to the invention is being worn, the two air cushion strips 6 produce a massaging action on both sides of the thoracic vertebral column and if need be also on both sides of the upper lumbar vertebral column, wherein the air cushion strips 6 are fixed by means of the article of clothing 1. Even with slight body movements, the air chambers 8 promote improved circulation by means of their massaging action, wherein depending on posture, the air in the different air chambers can move and as a result, can adapt to the anatomy of the user. This is particularly true when the air cushion strips 6 are not filled full, but are only filled for example two-thirds full so that the air can always move through the breaks 9 into other air chambers 8 in which the stress is lower or is at its lowest. In this connection, the article of clothing 1 should also correspond to the usual wearing habits of a corselet and should exert a light, circular, elastic pressure on the body or should transmit this pressure to the body via the air chambers 8.

In its lower region, the device 11 can also be provided with a pocket 19 for an intrinsically known lumbosacral truss pad in order to also make use of its action.

The invention produces the surprising advantage that in contrast to the lumbosacral truss pads, the air cushion strips 6 predominantly act in the sense of promoting circulation. Therefore they encourage not only the combination therapy explained at the beginning but they also increase the transmission of substances administered for the treatment of osteoporosis via the bloodstream into the bones even with comparatively slight bodily movements, i.e. without specific exercises.

The invention is not limited to the exemplary embodiment described, which could be modified in a number of ways. In lieu of the above-described corselet, articles of clothing can be provided e.g. in the form of a body suit, a one-piece bathing suit, a pantsuit, coveralls, or the like, provided that they are conceived and/or designed so that they press the air cushion strips 6 against the body of the patient with the slight pressure desired. It is also clear that the air cushion strips 6 can be fastened to the respective article of clothing 1 in a manner different from the one shown and/or can be combined with a device different from the device 11 described, which could, for example, also have two separate pockets 14 without the common carrier 12. Furthermore, the air cushion strips 6 can be permanently filled with air, in which case the connection fittings 10 (valves) can be eliminated. Moreover, the inner surfaces of the air cushion strips 6 which come to rest against the body or the pocket(s) 14 that contain them can be provided with nubs or other raised, protruding in order to thereby increase or intensify the stimulation of mechanoreceptors/proprioceptors. In order to locally intensify the acting pressure of the air cushion strips 6, the ends of two or more belts or restraints can be fastened to the backside of the article of clothing 1 and, after the article of clothing 1 is put on, can be moved forward and cinched more or less tightly and connected to one another by means of hook-and-loop elements or other means. The ends of these restraints are preferably attached approximately in the vicinity of the center line 5 and are attached to the outside of the article of clothing 1. Furthermore, for each article of clothing, more than one air cushion strip can be provided on each side of the vertebral column and/or the air cushion strips can be embodied in a different manner than the one shown. Moreover, all of the articles of clothing and/or air cushion strips can be produced in different sizes in order to accommodate the different body sizes of the patients. Finally, it should be evident that the above-described features can also be used in different combinations than the ones depicted and described above.

What is claimed is:

1. An article of clothing for osteoporosis treatment being made from a flexible, stretchable material and comprising: a front part (2), a back part (3) having an inner side and an imaginary center line (5) associated with a verbal column of a user, and at least two air cushion strips (6) extending over a thoracic vertebral region of said user, wherein one of said cushion strips (6) is on one side of said imaginary center line (5) and another one of said cushion strips (6) is on another side of said imaginary center line (5) and wherein each of said cushion strips (6) has a plurality of air chambers (8) being separated from one another by means of discontinuous seams (7) such that said air chambers (8) communicate with one another.

2. An article according to claim 1, wherein said air cushion strips (6) are disposed in pockets (14) attached to said inner side.

3. An article according to claim 2, wherein said pockets (14) are fastened to said inner side by means of hook-and-loop strips (18).

4. An article according to claim 2, wherein said pockets (14) are provided on a common carrier (12) and wherein said carrier (12) is fastened to said back part (3).

5. An article according to claim 4, wherein said carrier (12) is fastened to said back part (3) by means of hook-and-loop strips (18).

6. An article according to claim 1 and further being embodied in the form a body, suit, corselet, coveralls, pantsuit or one-piece bathing suit.

7. An article of clothing for osteoporosis treatment being made from a flexible, stretchable material and comprising: a front part (2), a back part (3) having an inner side and an imaginary center line (5) associated with a vertebral column of a user, a common carrier (12) fastened to said inner side of said back part (3), pockets (14) attached to said common carrier (12) and at least two air cushion strips (6) being disposed in said pockets (14) and extending over a thoracic vertebral region of said user, wherein one of said cushion strips (6) is on one side of said imaginary center line (5) and another one of said cushion strips (6) is on another side of said imaginary center line (5) and wherein each of said cushion strips (6) has a plurality of air chambers (8) communicating with one another.

8. An article according to claim 7, wherein said pockets (14) are provided with closure elements (15, 16).

9. An article according to claim 8, wherein said closure elements (15, 16) include hook-and-loop strips.

10. An article according to claim 6 and further being embodied in the form of a body, suit, corselet, coveralls, pantsuits or one-piece bathing suit.

11. An article of clothing for osteoporosis treatment being made from a flexible, stretchable material and comprising: a front part (2), a back part (3) having an inner side and an imaginary center line (5) associated with a vertebral column of a user, and at least two air cushion strips (6) extending over a thoracic vertebral region of said user, wherein one of said cushion strips (6) is on one side of said imaginary center line (5) and another one of said cushion strips (6) is on another side of said imaginary center line (5), and wherein each of said cushion strips (6) has a plurality of air chambers (8) being separated from but communicating with one another.

12. An article according to claim 11 and further being embodied in the form of a body, suit, corselet, coveralls, pantsuit or one-piece bathing suit.

13. An orthopedic device for osteoporosis treatment, comprising: a flexible carrier (12) being designed for being fastened to an inner side of a back part (3) of an article of clothing (1) and having a back face and a front face, said back face having means (18) for fastening said carrier (12) to said back part (3) and said front face having an imaginary center line (5) associated with a vertebral column of a user and two pockets (14) attached to said carrier (12), one pocket (14) being on one side of said imaginary center line (5) and another one of said pockets (14) being on another side of said imaginary center line (5), and at least two air cushion strips (6) for being inserted into said pockets (14), each of said cushion strips (6) having a plurality of air chambers being separated from and communicating with one another.

* * * * *